United States Patent
Nunez et al.

(10) Patent No.: US 9,060,952 B2
(45) Date of Patent: Jun. 23, 2015

(54) SYNERGISTIC PRESERVATIVE BLENDS

(75) Inventors: Rosita Nunez, Nutley, NJ (US); Larry Kent Hall, Easton, PA (US); Crystal Maira, Baldwinsville, NY (US); Joseph Kimler, Yardville, NJ (US); Craig Carter, Macungie, PA (US)

(73) Assignee: LONZA LTD., Basel (CH)

( * ) Notice: Subject to any disclaimer, the term of this patent is extended or adjusted under 35 U.S.C. 154(b) by 662 days.

(21) Appl. No.: 12/996,044

(22) PCT Filed: May 20, 2009

(86) PCT No.: PCT/EP2009/003610
§ 371 (c)(1),
(2), (4) Date: Feb. 25, 2011

(87) PCT Pub. No.: WO2009/146800
PCT Pub. Date: Dec. 10, 2009

(65) Prior Publication Data
US 2011/0301206 A1    Dec. 8, 2011

Related U.S. Application Data

(60) Provisional application No. 61/058,362, filed on Jun. 3, 2008.

(30) Foreign Application Priority Data

Aug. 15, 2008    (EP) .................................... 08014560

(51) Int. Cl.
| | |
|---|---|
| *A61K 8/34* | (2006.01) |
| *A61K 8/36* | (2006.01) |
| *A61K 8/49* | (2006.01) |
| *A61Q 19/00* | (2006.01) |

(52) U.S. Cl.
CPC . *A61K 8/49* (2013.01); *A61K 8/342* (2013.01); *A61K 8/345* (2013.01); *A61K 8/36* (2013.01); *A61K 8/4926* (2013.01); *A61K 8/498* (2013.01); *A61K 2800/524* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 4,404,197 | A * | 9/1983 | Fox et al. ...................... | 514/157 |
| 5,100,656 | A | 3/1992 | Lang et al. | |
| 5,618,545 | A * | 4/1997 | Orita et al. ................... | 424/401 |
| 2006/0106024 | A1* | 5/2006 | Levy et al. ................... | 514/250 |
| 2009/0117061 | A1* | 5/2009 | Gross ............................ | 424/59 |

FOREIGN PATENT DOCUMENTS

DE    0 365 825    5/1990

OTHER PUBLICATIONS

Ash, Handbook of Preservatives, Synapse Information Resources, Inc., 2004, p. 434.*
Balatsouras et al., Chemical Preservatives as Inhibitors of Yeast Growth, Journal of Food Science, vol. 28, Issue 3, pp. 267-275, May 1963.*
Kabara, Fatty Acids and Derivatives as Antimicrobial Agents, Antimicrob. Agents Chemother. 1972, 2(1): 23.*

* cited by examiner

Primary Examiner — Svetlana M Ivanova
(74) Attorney, Agent, or Firm — Hoffmann & Baron, LLP

(57) ABSTRACT

The present invention is a preservative formulation which includes a combination of at least two (2) compounds having bactericidal and/or fungicidal properties wherein the at least two (2) compounds is selected from the group consisting of methylisothiazolinone/piroctone olamine; caprylyl glycol/dehydroacetic acid; undecanol/dehydroacetic acid and lauryl alcohol/sorbic acid. The invention also includes preparations including such combination as well as a method of using the combination to reduce bacterial and fungal load of preparations.

8 Claims, No Drawings

SYNERGISTIC PRESERVATIVE BLENDS

This application is the U.S. National Phase of, and Applicants claim priority from, International Application Number PCT/EP2009/003610 filed 20 May 2009, European Patent Application bearing Serial Number 08014560.0 filed 15 Aug. 2008 and U.S. Provisional Patent Application No. 61/058,362 filed 3 Jun. 2008, which are incorporated herein by reference in their entirety.

BACKGROUND OF THE INVENTION

The present invention discloses synergistic preservative formulations comprising bactericidal and fungicidal compounds, a method of reducing the bacterial and fungal load of a preparation as well as the use of the synergistic preservative formulations according to the invention for reducing the bacterial and fungal load of preparations.

A wide variety of personal, household and industrial products, formulations and preparations need to be protected from contamination with bacteria and fungi. This is usually achieved by adding formaldehyde releasers and/or parabens because of the good bactericidal and fungicidal properties of these compounds.

However, these compounds of the state of the art suffer from some severe drawbacks, namely that their preservation capacity is so high that its effect continues even after, e.g. in case of a lotion, it is applied onto the skin, absorbed, distributed through the blood and deposited in the major organs of the body. Since formaldehyde and parabens impair enzyme function, there is the possibility of interference with the normal human cell and organ function.

DESCRIPTION OF THE INVENTION

Therefore, the technical problem to be solved by the present invention is to provide preservative formulations that avoid the disadvantages of those according to the state of the art. This problem is solved by reducing the necessary concentration of the formulation while still maintaining microbe control through the surprising and unexpected synergistic cooperation of at least two compounds.

It is therefore one object of the present invention to provide a preservative formulation comprising the combination of at least two compounds having bactericidal and/or fungicidal properties, wherein the respective combination is selected from the group consisting of methylisothiazolinone/piroctone olamine; caprylyl glycol/dehydroacetic acid; undecanol/dehydroacetic acid and lauryl alcohol/sorbic acid.

The bactericidal compound is preferably present in a concentration of 1% to 5%, when the bactericidal compound is a methylisothiazolinone, and 25% to 75% when it is caprylyl glycol, undecanol and lauryl alcohol. Even more preferred, the bactericidal compound is present in a concentration of 1.5% to 3% when it is a methylisothiazolinone, and 30% to 70% when it is caprylyl glycol, undecanol and lauryl alcohol.

The fungicidal compound is preferably present in a concentration of 25% to 99%. Even more preferably, the fungicidal compound according to the invention is present in a concentration of 30% to 95%.

All percentages are weight percentages unless otherwise stated.

The preferred isomer of methylisothiazolinone is 2-methylisothiazolin-3-one. However, other isomers are also within the scope of the invention.

It may be preferred that the preservative formulations according to the invention are combined with appropriate solvents. Preferably, said solvents are selected from the class of glycols. Most preferably, said solvents are selected from the group consisting of propylene glycol, butylene glycol and pentylene glycol.

The method of reducing the bacterial and fungal load of a preparation according to the present invention preferably comprises adding a preservative formulation comprising at least two compounds having bactericidal and/or fungicidal properties to the preparation to be conserved. The preferred bactericidal and fungicidal compounds, their preferred concentrations and combinations are as stated above.

Generally, the preparations according to the invention can be added to a wide variety of personal, household and industrial products, formulations and preparations.

Preferred preparations according to the invention are selected from the group consisting of cosmetic preparations such as lotions, creams, salves and ointments, cleaners, detergents, feminine hygiene products, wipes, pet care preparations, hair preparations such as shampoos, conditioners, gels, fixatives and sprays.

Another object of the present invention is the use of the synergistic preservative formulations according to the invention for reducing the bacterial and fungal load of preparations. All details regarding the preferred bactericidal and fungicidal compounds, their preferred concentrations and combinations as well as the preferred preparations where the synergistic preservative formulations can be applied are the same as those given above.

The invention will now be described by way of the following, non-limiting examples.

EXAMPLE 1

Preservative challenge testing was done to evaluate the performance of the blends in finished cosmetic preparations. Testing was conducted in a shampoo and a lotion base as described herein. A standardized mixed bacterial culture was prepared as follows. Three individual Tryptic Soy Agar slants of *Staphylococcus aureus* (ATCC 6538), *Escherichia coli* (ATCC 8739) and *Pseudomonas aeruginosa* (ATCC 9027) were incubated at approximately 35° C. for ~24 hours. Each slant was then washed with 5 mL of sterile Phosphate Buffered Dilution Water (PBDW). The 5 mL was transferred to an additional 5 mL of BPDW for a total 10 mL individual bacterial suspension. The absorbance of each individual suspension was measured spectrophotometrically at 530 nm after calibration of the instrument with a blank of PBDW. Each individual suspension was standardized to ~$10^9$ CFU/mL. Five mL was aseptically transferred from each individual suspension to one sterile specimen cup to create the "Mixed Bacteria". Then 40 g of each shampoo and lotion sample was inoculated with 0.2 mL of the standardized bacterial solution and each sample was mixed well.

Two individual Sabouraud Agar slants of *Candida albicans* (ATCC 10231), and three Sabouraud Agar plates of *Aspergillus niger* (ATCC 16404) were incubated at approximately 30° C. for ~24 hours and 5 days, respectively. The *Candida* slant was then washed with 5 mL of sterile Phosphate Buffered Dilution Water (PBDW). The 5 mL was transferred to an additional 5 mL of BPDW for a total 10 mL individual *Candida* suspension. For the *Aspergillus*, a sterile cotton swab was immersed into a 10 mL tube of sterile PBDW and then dipped into a sterile tube of Tween 80. The swab was then run back and forth across each of the *Aspergillus* plates, transferring the spores to the 10 mL PBDW tube in between each spore removal process. One mL from each of the suspensions was transferred to a separate 9 mL PBDW tube. Each of these 1:9 suspensions was measured on a hemacytomter and the original suspensions were standardized to ~$10^7$ cells/mL. Seven mL was aseptically transferred from each individual suspension to one sterile specimen cup to create the "Mixed Fungi". Then 40 g of each shampoo and lotion sample was inoculated with 0.4 mL of the standardized fungal solution and each sample was mixed well.

At days 0, 7, 14 and 28 days, sampling was done as follows. One gram of each sample was aseptically transferred to a separate 9 mL D/E neutralizing broth tube to form the $10^{-1}$ dilution. Serial dilutions were prepared through to a $10^{-6}$ dilution in BPDW. The serial dilutions for the bacterial cultures were plated by pour plate with Tryptic Soy Agar and incubated at ~35° C. for 48 hours. Serial dilutons for the fungal samples were plated by pour plate with Sabouraud Agar and incubated at ~30° C. for 72 hours. Plates were enumerated after the incubation period. Results are shown in Tables 1 and 2. The blends were effective in significantly reducing the bacterial and fungal counts over a 28 day period.

TABLE 1

Preservative Challenge Data
Mixed Bacterial Counts (CFU/gram)

| Test Samples | Day 0 | Day 7 | Day 14 | Day 28 |
|---|---|---|---|---|
| Unpreserved lotion | $1.0 \times 10^7$ | $1.3 \times 10^5$ | $1.4 \times 10^4$ | $1.4 \times 10^3$ |
| Lotion + 95 ppm methylisothiazolinone + 0.5% piroctone olamine | $1.7 \times 10^7$ | <10 | <10 | <10 |
| Lotion + 1% Caprylyl glycol + 0.5% Dehydroacetic acid | $1.1 \times 10^7$ | <10 | <10 | <10 |
| Lotion + 0.5% undecanol + 0.5% Dehydroacetic acid | $1.3 \times 10^7$ | <10 | <10 | <10 |
| Unpreserved Shampoo | $9.2 \times 10^6$ | $2.5 \times 10^7$ | $2.0 \times 10^7$ | $2.2 \times 10^6$ |
| Shampoo + 0.5% lauryl alcohol + 0.5% sorbic acid | $1.2 \times 10^7$ | <10 | <10 | <10 |

Inoculum:
Mixed Bacteria - approximately equal amounts of *P. aeruginosa*, *S. aureus* and *E. coli*. $9 \times 10^5$ to $5.5 \times 10^6$

TABLE 2

Preservative Challenge Data
Mixed Fungal Counts (CFU/gram)

| Test Samples | Day 0 | Day 7 | Day 14 | Day 28 |
|---|---|---|---|---|
| Unpreserved lotion | $5.0 \times 10^5$ | $2.1 \times 10^5$ | $3.2 \times 10^5$ | $1.1 \times 10^4$ |
| Lotion + 95 ppm methylisothiazolinone + 0.5% piroctone olamine | $1.0 \times 10^5$ | <10 | <10 | <10 |
| Lotion + 1% Caprylyl glycol + 0.5% Dehydroacetic acid | $2.0 \times 10^5$ | <10 | <10 | <10 |
| Lotion + 0.5% undecanol + 0.5% Dehydroacetic acid | $1.2 \times 10^5$ | <10 | <10 | <10 |
| Unpreserved Shampoo | $9.8 \times 10^5$ | $2.1 \times 10^5$ | $2.6 \times 10^4$ | $3.4 \times 10^3$ |
| Shampoo + 0.5% lauryl alcohol + 0.5% sorbic acid | $3.0 \times 10^5$ | <10 | <10 | <10 |

Inoculum:
Mixed Fungi - approximately equal amount of *C. albicans* and *A. niger*. $6.9 \times 10^4$ to $1.2 \times 10^5$

EXAMPLE 2

Minimum inhibitory concentrations (MIC) were determined for individual components and binary formulations as follows. Individual bacterial suspensions of *S. aureus* (gram positive), *E. coli* and *P. aeruginosa* (both gram negative) and individual fungal suspensions of *C. albicans* and *A. niger* were prepared as described in Example 1. Each individual suspension was standardized with PBDW to yield a ~$10^8$ CFU/mL or ~$10^7$ cells/mL for the individual bacteria and fungi, respectively.

The individual components and binary formulations were diluted in either DI water or propylene glycol (as appropriate for solubility) to yield a 10,000 ppm total starting active solution. From the 10,000 ppm solution, a 1:9 dilution was made in sterile Nutrient Broth to yield a 1,000 ppm active solution. Five mL of the 1,000 ppm dilution was transferred to five mL of sterile Nutrient Broth (NB) to yield a 500 ppm active solution. This dilution scheme was repeated down to 3.90 ppm active. The same dilutions were made in sterile Sabouraud Dextrose Broth (SDB) for the fungal MIC testing. The series of nine active solutions (3.9 ppm~1000 ppm) was prepared for each of the five microorganisms to be tested.

From the *E. coli* suspension, 0.1 mL was added to each of the nine, 5-mL active solutions in NB. Each tube was mixed thoroughly. This was repeated for each of the bacterial suspensions. Similarly, 0.1 mL of the *C. albicans* suspension was added to each of the nine, 5-mL active solutions in SDB. This was repeated with *A. niger* in a separate set of dilutions. Each tube was mixed thoroughly. Controls were prepared for each organism by inoculating 5 mL of NB or SDB, as appropriate. All three sets of bacterial tubes were incubated at 35° C. for 48 hours and the two sets of fungal tubes were incubated at 30° C. for 72 and 120 hours. At the end of the incubation period, the tubes were mixed and visually inspected for turbidity compared to the control. The lowest concentration with a lack of turbidity was recorded as the Minimum Inhibitory Concentration (MIC). The results are shown in Tables 3 and 4.

The synergism value is $(Q_A/Q_a + Q_B/Q_b)$. $Q_A$ is the concentration of component A in the mixture, $Q_a$ is the concentration of component A applied singly, $Q_B$ is the concentration of component B in the mixture, $Q_b$ is the concentration of component B applied singly. When the synergism value is less than one, the mixture is synergistic. Values for $(Q_A/Q_a + Q_B/Q_b)$ of 1 and greater than 1 represent an additive effect and an antagonistic effect, respectively.

TABLE 3

MIC values (in ppm) for preservative formulations versus bacteria

| | Organism type | | |
|---|---|---|---|
| | Gram (+) | Gram (−) | Gram (−) |
| | Organism name | | |
| | S. aureus | P. aeruginosa | E. coli |
| ATCC strain number | 6538 | 9027 | 8739 |
| Caprylyl Glycol and Dehydroacetic acid blend | 500 | 500 | 500 |
| $Q_A$ | 250 | 250 | 250 |
| $Q_a$ | >1000 | >1000 | 1000 |
| $Q_B$ | 250 | 250 | 250 |
| $Q_b$ | 500 | 500 | 500 |
| $Q_A/Q_a + Q_B/Q_b$ | <0.75 | <0.75 | 0.75 |
| Undecanol and Dehydroacetic acid blend | 1,000 | 500 | 1,000 |
| $Q_A$ | 500 | 250 | 500 |
| $Q_a$ | >1000 | >1000 | >1000 |
| $Q_B$ | 500 | 250 | 500 |
| $Q_b$ | 500 | 500 | 500 |
| $Q_A/Q_a + Q_B/Q_b$ | <1.5 | <0.75 | <1.5 |

TABLE 4

MIC values (in ppm) for preservative formulations versus bacteria, yeast and fungus formulations with piroctone olamine

| | Gram (+) | Gram (−) | Gram (−) | Mold | Yeast |
|---|---|---|---|---|---|
| | \multicolumn{5}{c}{Organism name} | | | | |
| | S. aureus | P. aeruginosa | E. coli | A. niger | C. albicans |
| ATCC strain number | 6538 | 9027 | 8739 | 16404 | 10231 |
| Methylisothiazolinone and Piroctone Olamine blend | 31.25 | 31.25 | 31.25 | 7.81 | 7.81 |
| $Q_A$ | 15.63 | 15.63 | 15.63 | 3.91 | 3.91 |
| $Q_a$ | 250 | 62.5 | 62.5 | 500 | 250 |
| $Q_B$ | 15.63 | 15.63 | 15.63 | 3.91 | 3.91 |
| $Q_b$ | 62.5 | 62.5 | 62.5 | 62.5 | 62.5 |
| $Q_A/Q_a + Q_B/Q_b$ | 0.31 | 0.5 | 0.5 | 0.07 | 0.08 |

The invention claimed is:

1. A preservative formulation comprising a combination of a bactericidal compound and a fungicidal compound in a synergistically effective concentration, wherein the respective combination is selected from the group consisting of methylisothiazolinone/piroctone olamine; caprylyl glycol/dehydroacetic acid; undecanol/dehydroacetic acid and lauryl alcohol/sorbic acid.

2. The formulation according to claim 1, wherein the bactericidal compound is present in a concentration of 1% to 5%, when the bactericidal compound is methylisothiazolinone, and 25% to 75% when the bactericidal compound is caprylyl glycol, undecanol and lauryl alcohol.

3. The formulation according to claim 2, wherein the bactericidal compound is present in a concentration of 1.5% to 3% when the bactericidal compound is methylisothiazolinone, and 30% to 70% when the bactericidal compound is caprylyl glycol, undecanol and lauryl alcohol.

4. The formulation according to claim 1, wherein the fungicidal compound is present in a concentration of 25% to 99%.

5. The formulation according to claim 4, wherein the fungicidal compound is present in a concentration of 30% to 95%.

6. A method of reducing the bacterial and fungal load of a preparation comprising adding the preservative formulation according to claim 1 to the preparation.

7. The method according to claim 6, wherein the preparation is selected from the group consisting of personal, household and industrial products, formulations and preparations.

8. The method according to claim 7, wherein the preparation is selected from the group consisting of cosmetic preparations such as lotions, creams, salves and ointments, cleaners, detergents, feminine hygiene preparations, wipes, pet care preparations, hair preparations such as shampoos, conditioners, gels, fixatives and sprays.

* * * * *